United States Patent
Chen

(10) Patent No.: US 7,378,235 B2
(45) Date of Patent: May 27, 2008

(54) **METHOD FOR SCREENING COMPOUNDS AGAINST *FLAVIVIRUSES* BY USING PERSISTENT VIRUS-INFECTED CELL SYSTEM**

(75) Inventor: Li-Kuang Chen, Taiwan (CN)

(73) Assignee: Buddhist Tzu Chi General Hospital, Hualien (TW)

( * ) Notice: Subject to any disclaimer, the term of this patent is extended or adjusted under 35 U.S.C. 154(b) by 0 days.

(21) Appl. No.: 11/210,183

(22) Filed: Aug. 22, 2005

(65) Prior Publication Data

US 2006/0188894 A1    Aug. 24, 2006

(30) Foreign Application Priority Data

Feb. 24, 2005    (TW) .............................. 94105533 A

(51) Int. Cl.
*C12Q 1/70* (2006.01)
*C12Q 1/18* (2006.01)

(52) U.S. Cl. ............................................ 435/5; 435/32
(58) Field of Classification Search .................... 435/5, 435/6, 7.1; 424/188.1, 212.1, 228.1
See application file for complete search history.

(56) References Cited

U.S. PATENT DOCUMENTS

2005/0048073 A1 * 3/2005 De Groot et al. ......... 424/186.1

OTHER PUBLICATIONS

Houghton et al. "Prospects for a vaccine against the hepatitis C virus," Nature, vol. 436, Aug. 18, 2005☐☐.*
Liao et al., "Antiapoptotic but Not Antiviral Function of Human bcl-2 Asists Establishment of Japanese Encephalitis Virus Persistence in Cultured Cells," Journal of Virology, vol. 72, No. 12, p. 9844-9854 (1998).*
Pugachev et al., "New developments in flavivirus vaccines with special attention to yellow fever," Curr. Opin. Infect. Dis. 18:387-394 (2005).*
Rossi et al., "Adaptation of West Nile virus replicons to cells in culture and use of replicon-bearing cells to probe antiviral action," Virology, 331, 457-470 (2005).*
Shi et al. ("Strategies for the identification of inhibitors of West Nile virus and other flaviviruses, Curr Opin Investig Drugs," 3(11): 1567-73 (2002)).*

* cited by examiner

*Primary Examiner*—Mary E. Mosher
(74) *Attorney, Agent, or Firm*—Edwards Angell Palmer & Dodge LLP; Peter F. Corless; Dwight D. Kim

(57) ABSTRACT

This invention provides a method for screening compounds against *Flavivirus*. More specifically, this invention provides a method for screening compounds against *Flaviviruses* by using a persistent virus-infected cell system, including (a) establishment of persistent virus-infected cell lines, (b) preparation of monoclonal antibody by using said persistent virus-infected cell lines, (c) incubation of tested compounds with said persistent virus-infected cell lines, (d) determination of the inhibition effect of tested compounds or vaccines on *Flavivirus* by sandwich ELISA using said monoclonal antibody.

11 Claims, 2 Drawing Sheets

FIG. 3

METHOD FOR SCREENING COMPOUNDS AGAINST *FLAVIVIRUSES* BY USING PERSISTENT VIRUS-INFECTED CELL SYSTEM

FIELD OF THE INVENTION

This invention relates to methods for screening compounds against virus infection, and more particularly, to a method for screening compounds against *Flaviviruses* by using a persistent virus-infected cell system.

BACKGROUND OF THE INVENTION

*Flaviviridae* family comprises three genuses of *Flavivirus, Pestivirus*, and *Hepacivirus*. Genus *Flavivirus* genomes consist of a linear, single-stranded, positive sense RNA having a total genome range of 10 to 11 kilobase pairs, which forms a structure of 5'-stuctural genes-nonstructural genes-3'. The 3' terminus of *Flavivirus* genomes is not polyadenylated, and the 5' end has a methylated nucleotide cap (allowing for translation) or a genome-linked protein. Virus structural genes on 5'-end occupy one-fourth of the whole genome, which comprises C, prM, and E genes, and non-structural genes occupy the remaining parts of the genome. The virions appear roughly as spheres, 40-65 nm in diameter comprising three structural proteins: truncated envelope protein (E protein), membrane protein (M protein), and capsid protein (C protein). The number of viral non-structural proteins existing in *Flavivirus*-infected cells is not quite sure. However there are at least three non-structural proteins identified in *Flavivirus*-infected cells and those proteins are highly related to viral RNA replication, wherein at least one protein has a proteinase function. Truncated envelope protein (E protein) is a viral agglutinin that will allow infected cells to adhere hemoglobin. The 5'-UTR (un-translated region) is a highly conserved region in viral genome and an important part in the initiation or control of protein translation (Thurner C., et al., J Gen Virol. 2004 May; 85(Pt 5): 1113-24; Henchal E. A. and Putnak J. R. Clin Microbiol Rev. 1990 October; 3(4): 376-396; Chambers T. J. et al., Annu Rev Microbiol. 1990; 44:649-88.)

Genus *Flavivirus* comprises at least 65 species being either direct pathogens for humans or zoonosis. Except for the hepatitis C virus, which is spread by body fluid contact, the media for other viruses are arthropods such as mosquitoes or ticks. There are three clinical syndromes observed for *Flavivirus* infection including: central neuron disease caused by *Flavivirus* such as St. Louis encephalitis, murray valley encephalitis, Japanese encephalitis, and the like; systematic disorder caused by yellow fever virus infecting organs; and serious muscle disorders (such as acute flaccid paralysis (AFP), peripheral demyelinating process (Guillain-Barré Syndrome (GBS), anterior myelitis and the like), and hemorrhagic fever caused by West Nile virus, dengue fever virus, and the like). According to estimation from the World Health Organization (WHO), just for the dengue fever virus, about 2 million infections result every year globally. Over two thousand cases including 77 deaths have been reported for the West Nile virus infection from January to November of 2004 according to statistical data published by the CDC (USA) dated on Nov. 8, 2004. Flavivirus infection has become a major issue on worldwide epidemiology.

The infection of *Flavivirus* needs to be confirmed by virus isolation and serological identification; wherein yellow fever virus, dengue virus, and some encephalitis cases caused by ticks can be isolated from a blood sample. However, the serological identification of virus is not useful for therapy due to the low crossover antibody protection. Further, a vaccine for Japanese encephalitis has been widely used for years; however, because said vaccine is a live attenuated virus vaccine, there's a lime limitation for titer maintenance. In the past, people who had received vaccination used to obtain a natural boost due to frequently being bilten by mosquitoes. The chance to get a natural boost is lower today due to improved living conditions. Therefore, there are still some Japanese encephalitis infected cases reported from vaccinated adults. Currently, antiviral drugs are available for the treatment of HIV, herpes virus (pathogens for various diseases such as Herpes labialis or encephalitis), and hepatitis B or C viruses (both can result in liver cancer). There is no available or anticipated drug for the clinical treatment of *Flavivirus* infection, and syndrome supportive therapy has been applied in most cases. Therefore, it is urgently needed to have a simple and rapid method for screening natural or synthetic compounds that might be useful in preventing the *Flavivirus* infection.

The currently used screening method for anti-virus drugs comprises: infecting cells with virus, culturing the infected cells in a culture medium, adding possible compounds to the culture medium, and further examining the compounds to see which can decrease viral numbers. The above method is not economically efficient in that the laboratory staff needs to frequently repeat the step of infecting cells with virus. In addition, compounds selected by the above screening method are not guaranteed to inhibit intercellular viral protein expression. There are still some doubts as to whether or not the selected compounds can enter cells and the expressed cytoxicity on cells.

SUMMARY OF THE INVENTION

To solve the obstacles existing in current screening methods for drugs or lead compounds, this invention provides a screening method for compounds against *Flavivirus* infection, comprising the steps of: (a) establishment of persistent virus-infected cell lines, (b) preparation of monoclonal antibody by using said persistent virus-infected cell lines, (c) incubation of tested compounds with said persistent virus-infected cell lines, and (d) determination of the inhibition effect of tested compounds or vaccines on *Flavivirus* by sandwich ELISA using said monoclonal antibody.

The method for screening compounds against *Flavivirus* infection using the persistent virus-infected cell system of this invention comprises (a) establishment of persistent virus-infected cell lines, (b) preparation of monoclonal antibody by using said persistent virus-infected cell lines, (c) incubation of tested compound with said persistent virus-infected cell lines, (d) determination of the inhibition effect of tested compounds or vaccines on *Flavivirus* by sandwich ELISA using said monoclonal antibody.

For the monoclonal antibody used in the screening of this invention, it is preferable to have epitopes of non-structural protein (NS1 protein) or envelop protein (E protein), and, more preferably, a cocktail of these two monoclonal antibodies.

Compounds selected by using the screening method of this invention can be applied in the therapy and/or prophylaxis of *Flavivirus* infection.

Another embodiment of this invention is a kit for screening compounds against *Flavivirus* infection comprising: (a) materials to establish persistent virus-infected cell lines, (b) materials to prepare monoclonal antibody by using said persistent virus-infected cell lines, (c) guidelines for incubation of tested compound with said persistent virus-infected cell lines, (d) materials to determine the inhibition effect of tested compounds or vaccines on *Flavivirus* by sandwich ELISA using said monoclonal antibody. For the monoclonal antibody used in this embodiment, it is preferable to use epitopes of non-structural protein (NS1 protein) or envelop protein (E protein), and, more preferably, a cocktail of those two monoclonal antibodies.

Compounds selected by using the screening method of this invention can be applied in the preparation of medication for therapy and/or prophylaxis of *Flavivirus* infection.

*Flaviviruses* suitable for the screening method of this invention comprise Genus *Flavivirus* of *Flaviviridae*, comprising: Tick-borne viruses (such as Russian spring-summer virus, Omsk hemorrhagic fever virus, Powassan virus, Royal Farm virus, Karshi virus, Tick-borne encephalitis virus, Neudoerfl virus, Louping ill virus, Seabird tick-borne virus and the like), Mosquito-borne viruses (such as Aroa virus, Bussuquara virus, Iguape virus, Dengue virus (type 1 to 4), Kedougou virus, Japanese encephalitis virus, Cacipacore virus, Murray Valley encephalitis virus, Alfuy virus, St. Louis encephalitis virus, Usutu virus, West Nile virus, Kunjin virus, Yaounde virus, Kokobera virus, Stratford virus, Ntaya virus, Bagaza virus, Ilheus virus, Rocio virus, Israel turkey meningoencephalomyelitis virus, Tembusu virus, Spondweni virus, Zika virus, Yellow fever virus, Banzi virus, Bouboui virus, Edge Hill virus, Jugra virus, Saboya virus, Potiskum virus, Sepik virus, Uganda S virus, Wesselsbron virus and the like), viruses with no known arthropod vector(such as Entebbe virus, Entebbe bat virus, Sokoluk virus, Yokose virus, Modoc virus, Apoi virus, Cowbone Ridge virus, Jutiapa virus, San Perlita virus, Rio Bravo virus, Bukalasa bat virus, Carey Island virus, Dakar bat virus, Montana myotis leukoencephalitis virus, Phnom Penh bat virus, Batu Cave virus and the like).

The methods to establish the *Flavivirus* persistent infected cell lines can use the methods described in the publications (Virology. 217:220, J. V. 71:5963, J. V. 72:9844) or any other known methods used to prepare a persistent virus infected cell line. K562 cells can be used as the persistent virus-infected cells for the suspension cultivation, and BHK-21 cells, B2-5 cell line, and Bcl-2 expressing BHK-21 cells can be used for the attached cultivation. Cells will be infected with *Flavivirus* by incubation with virus. After most of the cytopathogenic effect (CPE) on the cells disappears, the rest of the proliferating cells will grow rapidly. The persistency of *Flaviviruses* infection is then assayed with IFA and ELISA by using the *Flavivirus*-specific monoclonal antibodies (described in this specification hereafter) as the primary antibody, and the FITC-conjugated (fluorescein isothiocyanate-conjugated) or HRP-conjugated (horseradish peroxidase-conjugated) goat-anti-mouse Ig antibody as the secondary antibody.

In the screening method of this invention, epitope of monoclonal antibody can be any epitope of *Flavivirus*, comprising E protein, C protein, and structural and non-structural proteins, wherein preferably it is composed of non-structural proteins. The monoclonal antibodies used in this invention are prepared by using hybridoma techniques comprising: (1) preparation of the conjugate of *Flavivirus* epitope and a carrier, wherein the conjugate is able to induce an immune reaction after immunization using said conjugate and an animal body, followed by collection of the antibody against *Flavivirus* epitope; (2) establishment of analysis system (IFA and ELISA) for determining immune reaction and screening animal sera or spleen cells having immune reaction; (3) Preparation and screening of hybridoma of animal spleen cells having *Flavivirus* epitope and myeloma; and (4) Production of a large amount monoclonal antibody by using said hybridoma.

Enzyme-linked immunosorbent assay (ELISA) used in the screening method of this invention can be the direct or indirect enzyme-linked immunosorbent assay, preferably the sandwich enzyme-linked immunosorbent assay. The condition of sandwich ELISA for each monoclonal antibody needs to be optimized.

BRIEF DESCRIPTION OF THE DRAWINGS

The present invention can be more fully understood by reading the following detailed description of the preferred embodiments, with reference made to the accompanying drawings, wherein:

Figure 3:
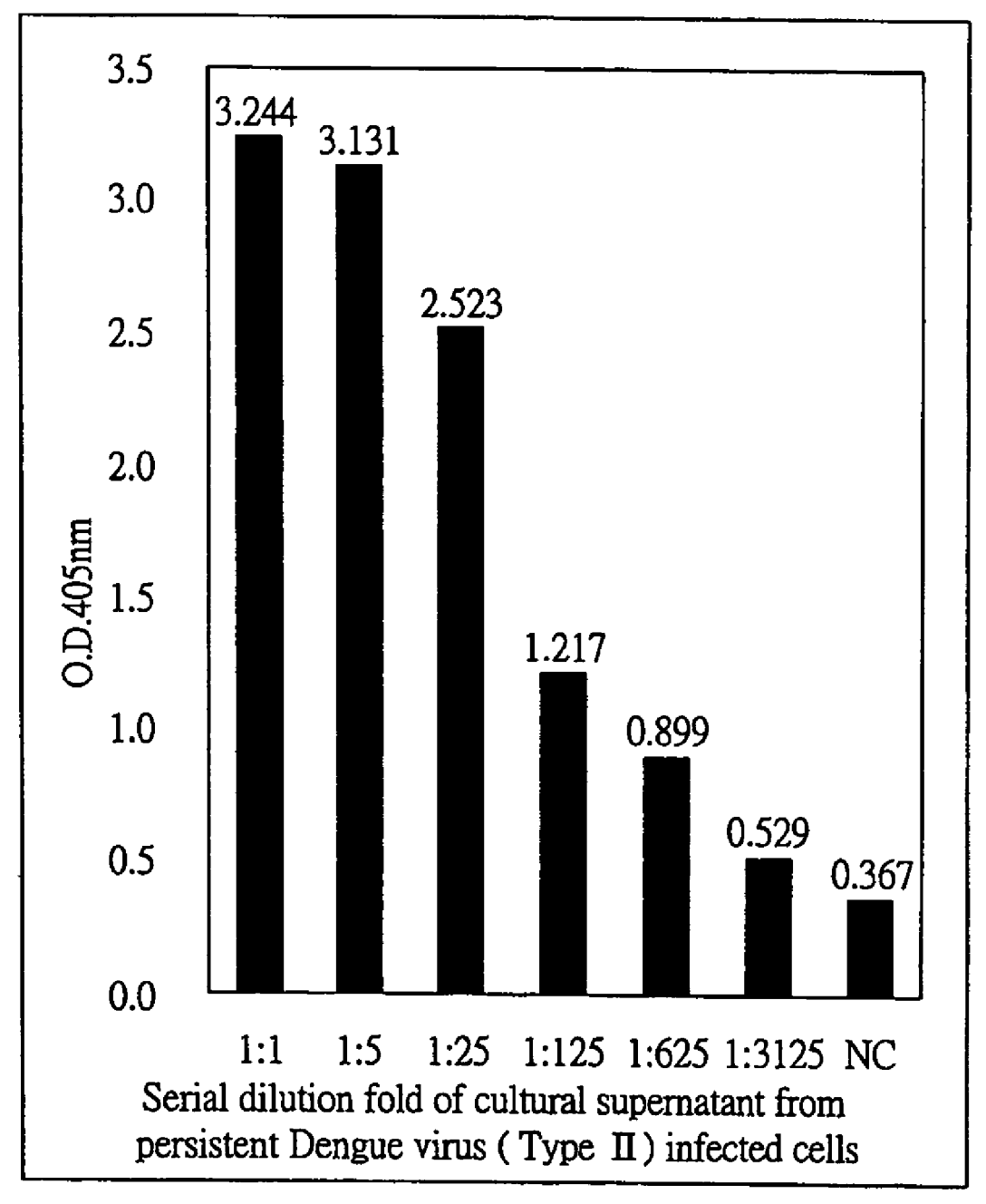

FIG. 3 is a schematic diagram showing the results of virus antigen content secreted in the supernatant of persistent dengue virus-infected (type 2) cell cultures by sandwich ELISA, wherein the virus antigen content in the supernatant of persistent virus-infected cell cultures established in this invention exhibits an increase of secreted viral antigen concentration.

DETAILED DESCRIPTION OF THE PREFERRED EMBODIMENTS

Establishment of Persistent *Flavivirus*-infected Cell Line

Figure 1:
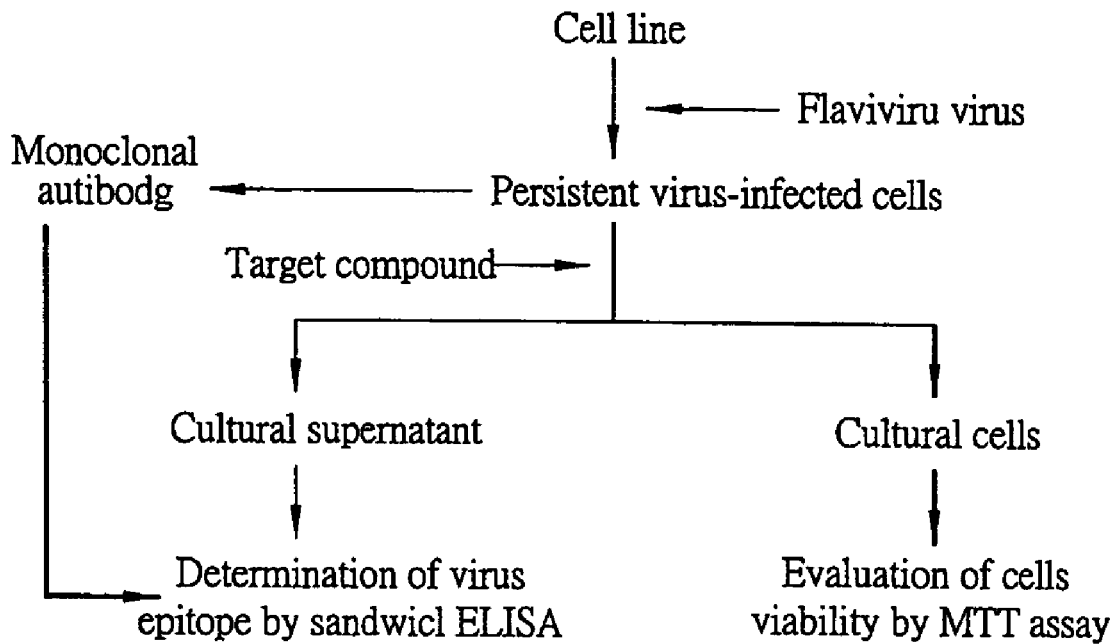
FIG. 1 is a schematic diagram showing the design of a compound screening system of this invention, wherein two parts are included in this system: establishment of a persistent virus-infected cell line and preparation of monoclonal antibody having epitope specificity with a hybridoma technique, and after addition of the tested compound to the persistent virus-infected cell, the supernatant of culture cell is subjected to sandwich ELISA for detection of viral antigen, and the culture cell can be subjected to MTT assay for determination of cytotoxic effect (viability)
Figure 2:
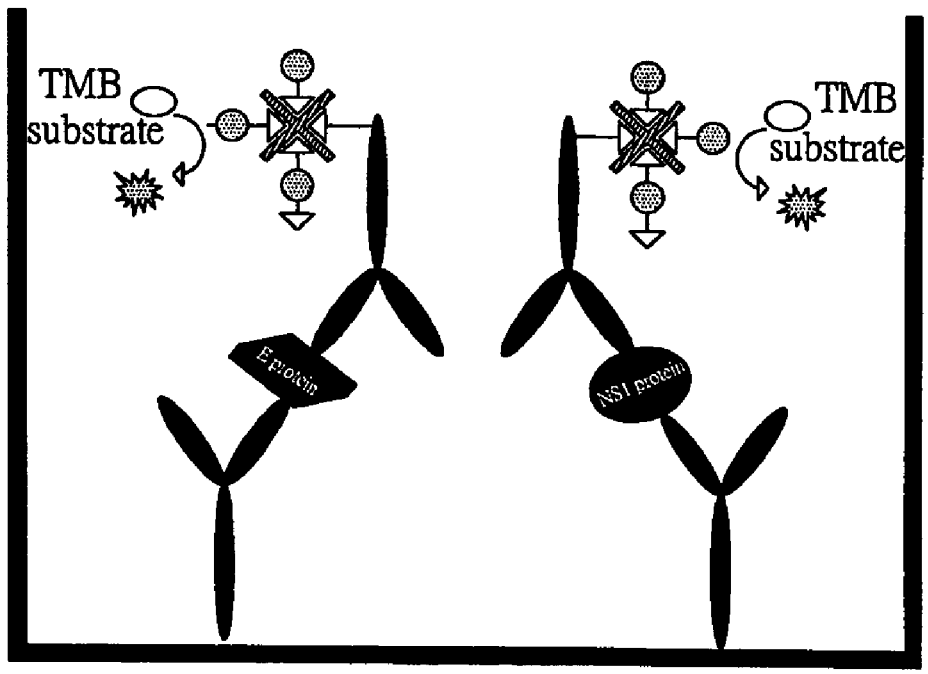
FIG. 2 is a schematic diagram showing the sandwich ELISA step of this invention, wherein in the sandwich ELISA step of this invention, primary antibodies and secondary antibodies both can use a cocktail of monoclonal antibodies having epitope specificity.

The methods to establish the persistent *Flavivirus*-infecied cell lines have been described in the publications (Virology. 217:220, J. V. 71:5963, J. V. 72:9844). Cells of B2-5 line, Bcl-2 expressing BHK-21 cells are infected with each type of *Flavivirus* (Table 1). After most of the cytopathogenic effect (CPE) on cells disappears, the rest of the proliferating cells will grow rapidly and the persistency of *Flaviviruses* infection is then assayed with IFA and ELISA by using the *Flavivirus*-specific monoclonal antibodies (described in this specification hereafter) as the primary antibody and the FITC-conjugated (fluorescein isothiocyanate-conjugated) or HRP-conjugated (horseradish peroxidase-conjugated) goat-anti-mouse Ig antibody as the secondary antibody.

Preparation of *Flavivirus*-specific Monoclonal Antibody by Hybridoma Technique

BALB/c mice were immunized with the supernatant of established persistent *Flaviviruses*-infected cell lines to increase the chance of getting a monoclonal antibody against the secreted viral proteins in culture supernatants. The *Flavivirus* strains used are listed in Table 1. After immunization, IFA and ELISA were used to check the specific antibody titers of the sensitized sera before cell fusion. The specific antibody (B cell) is fused with myeloma. B cell cannot be cultured long-term in a culture flask, and myeloma is a lymphoid tumor that can replicate and proliferate in a culture flask without time limit. These two cells were mixed and induced to fuse with each other by PEG (polyethylene glycol). Recombination may occur after these two sets of chromosomes are mixed, and then the chromosomes number might go back to normal after several cycles of mitosis. The daughter cells, called hybridoma, secrete the specific antibody and proliferate without limit. Once the target *Flavivirus*-specific monoclonal antibody produced by hybridoma was selected based on the characterization of monoclonal antibody, the production of antibody on large-scale can be accomplished by induction of ascites in NOD/SCID mice because of the low rate of contamination by natural immunoglobulin from host mice. Purification of the specific monoclonal antibodies from ascites was carried out by passing the ascites through the protein A or protein G column depending on isotype information from typing ELISA. The characterization of antigenic target molecules recognized by monoclonal antibodies can be confirmed from the molecular weight of the colored band by the Western blotting method.

TABLE 1

*Flaviviruses* strain used for preparation of monoclonal antibodies

| Virus | Strain Name | Source |
|---|---|---|
| Dengue Type 1 | HAWAII | ATCC |
| Dengue Type 2 | PLO46 | ATCC |
| Dengue Type 3 | H-87 | ATCC |
| Dengue Type 4 | H-241 | ATCC |
| West Nile | VR-1510 | ATCC |
| JEV (Japanese Encephalitis Virus) | RP9 | Home Lab |
| YFV (Yellow Fever Virus) | 17D | ATCC |

Optimization of Sandwich ELISA

The selection of monoclonal antibody to be used for sandwich ELISA was based on the ability of the monoclonal antibody to catch the viral protein in the supernatants of persistent virus-infected cells. The choice of the pair of primary and secondary antibodies was done through a competitive test to make sure the epitopes recognized by these two antibodies were different from each other. When there were more than one viral proteins secreted into the cultural supernatants, the primary antibody used for sandwich ELISA might be a cocktail of oligoclonal antibodies. The same principle was applied to choose the secondary antibody for the sandwich ELISA.

The detailed procedures for sandwich ELISA are described as follows: a cocktail of monoclonal antibodies against E and NS1 proteins of flavivirus used as primary antibody to capture secreted viral antigens was coated on the wells of ELISA-microplate at 4° C. and allowed to stand overnight. After washing with PBS containing 1% BSA (3 times) for blocking, the culture supernatants from persistent infected cells were added to microwells and the microplates were incubated at 37° C. for 90 minutes. After the microplates were washed with 1% BSA-containing PBS (3 times), a cocktail of paired biotin-conjugated secondary antibody was added to each well and the microplates were incubated at 37° C. for 90 minutes. The microplates were washed with PBS (3 times), then horseradish peroxidase-streptavidin was added to each well and the microplates were incubated at room temperature for 30 minutes. The microplates were washed with PBS (3 times) and TMB substrate was added to react for 30 minutes at room temperature. The results were readout at O. D. 405 nm with an ELISA-reader. Experiments on negative and positive control groups were done by using culture supernatants from mock or *Flavivoirus*-infected cytopathic BHK-21 cells.

Consistent Screening of Viral Antigen in Supernatants of Persistent *Flavivirus*-infected Cell Lines The viral antigens secreted into the supernatants of continuous long-term (up to 6 months) cultured persistent *Flavivirus*-infected cell lines could be directly detected by sandwich ELISA without any pre-treatments such as extraction or partial purification (FIG. 3). Furthermore, after 5 successive rounds of freezing for one week and cultivation for two weeks after thawing, the persistent *Flavivirus*-infected cell lines still secreted the same amount of viral antigens as at the beginning as detected by sandwich ELISA.

MTT assay

In the method of this invention, while the culture supernatants of cell lines was subjected to sandwich ELISA, the cultured cells can be separately subjected to MTT [3-(4,5-dimethylthiazol-2-yl)-2,5-diphenyl-2H-tetrazolium bromide (MTT)] assay to determine the cytotoxicity of the target compounds. MTT is a sensitive reagent for the measurement based upon the high reduction property of tetrazolium salt. Changes in cell proliferation activity caused by trophic factors, growth inhibitors, or inducers and inhibitors of apoptosis, can be quantified by the MTT assay. MTT is reduced to an insoluble formazan dye by mitochondria dehydrogenase enzymes associated with metabolic activity. The reduction of MTT is primarily due to glycolytic activity within the cells and is dependent upon the presence of NADH and NADPH. The formazan crystals must be dissolved with isopropanol and spectrophotometrically measured at 570 nm. The increase in MTF conversion is quantitatively proportional to the actively proliferating cells. Experiments on negative and positive control groups were conducted by using culture cells from mock or *Flavivirus*-infected cytopathic BHK-21 cell.

Design of the Compound Screening System

This cell-based screening system for searching for antiviral drugs from a library of pharmaceutical compounds comprises two components. One is a virus infection component for testing the effects of candidate chemicals added into the culture of persistent *Flavivirus*-infected cells. The supernatant is monitored by virus-specific sandwich-ELISA. Cytotoxic effects of the candidate chemicals are determined by checking viability of surviving cells by MTT assay. A simplified scheme of the design for the compound screening system is shown in FIG. 1.

The screening system of this invention has the following advantages: use of isotope is not necessary, no follow-up treatment is required for isotope waste; the screening system of this invention is applicable to a general microplate auto machine in a lab, new equipment is not needed; the establishment of persistent virus-infected cell lines can avoid virus instability and the repeated complicated operations for each preparation of virus infection; cytotoxic effect of compound can be determined by MTT assay at the same time as sandwich ELISA is performed; compounds selected from the screening method based on the use of persistent virus-infected cells will reveal the inhibition activity on the intercellular viral protein expression, and modifications are not necessary in order for compound to enter cells; viral-inhibition effects of the compounds selected by epilope specific monoclonal antibody is highly sensitive and not disturbed by other factors; a cocktail of monoclonal antibodies can be used in sandwich ELISA of this invention to detect various viral antigens simultaneously and to enhance the anti-viral accuracy of the selected compounds.

Interpretation of Screening Results

The interpretation of the results obtained by the method of this invention is straightforward. There is only one exceptional condition which should be ruled-out before making a conclusion, which is there is the possibility of interference involving antigen-antibody binding by the target compounds. This condition could be easily avoided by reducing OD values due to the target compounds negative control group right before sandwich ELISA determination.

The present invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A method for screening compounds against *Flavivirus*, comprising the steps of:
   (a) establishing persistent *Flavivirus*-infected cell lines;
   (b) preparing monoclonal antibody by using culture supernatants of said persistent *Flavivirus*-infected cell lines;
   (c) incubating test compounds with said persistent virus-infected cell lines; and
   (d) determining an inhibition effect of said test compounds on viral proteins secreted from said *Flavivirus*-infected cell lines by sandwich ELISA using said monoclonal antibody and determining cytotoxic effects on the said persistant virus-infected cell lines by MTT assay.

2. The method of claim 1, wherein said compounds are selected from natural compounds.

3. The method of claim 1, wherein said compounds are selected from synthetic compounds.

4. The method of claim 1, wherein said persistent virus-infected cell lines are established from suspension cell lines.

5. The method of claim 4, wherein said suspension cell lines are K562 cell lines.

6. The method of claim 1, wherein said persistent virus-infected cell lines are established from attached cell lines.

7. The method of claim 6, wherein said attached cell lines are selected from BHK-21 cell lines, B2-5 cell lines, or Bcl-2 expressed BHK-21 cell lines.

8. The method of claim 1, wherein said antibody used in said ELISA comprises one type of monoclonal antibody or a mixture of different types of monoclonal antibodies.

9. The method of claim 1, wherein said monoclonal antibody is against an epitope of said *Flavivirus*.

10. The method of claim 9, wherein said monoclonal antibody is against a non-structural (NS1) epitope of said *Flavivirus*.

11. The method of claim 9, wherein said monoclonal antibody is against an envelope protein (E protein) epitope of said *Flavivirus*.

* * * * *